United States Patent [19]
Wilson et al.

[11] Patent Number: 5,744,646
[45] Date of Patent: Apr. 28, 1998

[54] PREPARATION OF TRIS (PENTAFLUOROPHENYL) BORANE

[75] Inventors: David R. Wilson; Robert E. LaPointe, both of Midland, Mich.

[73] Assignee: The Dow Chemical Company, Midland, Mich.

[21] Appl. No.: 832,150

[22] Filed: Apr. 2, 1997

Related U.S. Application Data

[60] Provisional application No. 60/015,455 Apr. 15, 1996 and provisional application No. 60/015,821 Apr. 18, 1996.
[51] Int. Cl.$^6$ .................................................. C07F 5/02
[52] U.S. Cl. .................................................. 568/1
[58] Field of Search .................................................. 568/1

[56] References Cited

U.S. PATENT DOCUMENTS

| | | |
|---|---|---|
| 4,076,756 | 2/1978 | Nazarenko . |
| 5,600,004 | 2/1997 | Diefenbach .................................. 568/1 |

OTHER PUBLICATIONS

CA:121:109240, abs of EP604962, "Method of producing tris(pentafluorophenyl)borane using pentafluorophenyl alkali metal salt prepared from pentafluorobenzene", Ikeda, Jul. 7, 1994.

*Primary Examiner*—Gary Geist
*Assistant Examiner*—Jean F. Vollano

[57] ABSTRACT

A process for preparing tris(pentafluorophenyl)borane, the steps of the process comprising:

a) forming a pentafluorophenyl metal compound wherein the metal is selected from Group 11 or 12;

contacting the (pentafluorophenyl) metal compound from step a) with a boron halide compound to form tris (pentafluorophenyl)borane; and c) recovering the resulting tris(pentafluorophenyl)borane.

10 Claims, No Drawings

PREPARATION OF TRIS (PENTAFLUOROPHENYL) BORANE

CROSS REFERENCE STATEMENT

This application claims the benefit of U.S. Provisional application No. 60/015,455, filed Apr. 15, 1996, and U.S. Provisional application No. 60/015,821, filed Apr. 18, 1996.

BACKGROUND OF THE INVENTION

The present invention relates to a process for preparing tris(pentafluorophenyl)borane. Tris(pentafluorophenyl) borane is a strong Lewis acid having many useful industrial applications. In particular the compound is useful as a catalyst activator in combination with metallocene catalysts in Ziegler-Natta polymerizations.

It is previously known in the art to prepare zinc pentafluorobenzoate by contacting zinc hydroxide or zinc oxide with pentafluorobenzoic acid under dehydration conditions. It is further known to decarboxylate the zinc pentafluorobenzoate so formed thereby forming bis(pentafluorophenyl) zinc. *Chem. Ber.* 1967, 100, 3016-3023; *Organometal. Chem. Rev.*, 1966, 1, 279-304; *Chem. Ber.* 1967, 100, 2306-2311.

It is furthemore known to prepare tris(pentafluorophenyl) borane by decarboxylation of pentafluorobenzoic acid to form pentafluorobenzene, bromination of the pentafluorobenzene, formation of a pentafluorophenyl lithium compound or pentafluorophenyl magnesium compound from the bromopentafluorobenzene, and reaction with boron trihalide. The foregoing procedure is time consuming and not particularly efficient. Due to the multiple steps having reduced yields, the overall process is inefficient and wasteful of starting materials.

Accordingly, it would be desirable if there were provided an improved process for preparing tris(pentafluorophenyl) borane that has improved efficiency and greater industrial applicability.

SUMMARY OF THE INVENTION

According to the present invention there is now provided an improved process for preparing tris(pentafluorophenyl) borane, the steps of the process comprising:

a) forming a pentafluorophenyl metal compound wherein the metal is selected from Group 11 or 12;

b) contacting the (pentafluorophenyl) metal compound from step a) with a boron halide compound to form tris(pentafluorophenyl)borane; and c) recovering the resulting tris(pentafluorophenyl)borane.

In an additional embodiment of the invention, the initial step a) is performed by decarboxylation of a metal pentafluorobenzoate wherein the metal is selected from Group 11 or 12. The decarboxylation is preferably conducted by heating the metal pentafluorophenyl benzoate, preferably in a hydrocarbon liquid at a temperature from 100° to 500° C., optionally under reduced pressure. It has been discovered that the decarboxylation process can be carried out in high yield by the use of such hydrocarbon liquids. The alternative, prior art decarboxylation process utilizing sublimation under vacuum is difficult to practice in an industrial setting and yields are poor. On the other hand, the use of ethereal solvents requires a solvent change thereby complicating the synthesis and is therefor not desired.

DETAILED DESCRIPTION OF THE INVENTION

All references herein to elements or metals belonging to a certain Group refer to the Periodic Table of the Elements published and copyrighted by CRC Press, Inc., 1989. Also, any reference to the Group or Groups shall be to the Group or Groups as reflected in this Periodic Table of the Elements using the IUPAC system for numbering groups.

The improved process for preparing tris (pentafluorophenyl)borane disclosed herein most preferably comprises the steps of:

a1) forming a Group 11 or 12 metal pentafluorobenzoate by contacting pentafluorobenzoic acid with a Group 11 or 12 metal oxide or hydroxide under neutralization conditions and, optionally, dehydration conditions, or by contacting a Group 1 or 2 metal salt of pentafluorobenzoic acid with a Group 11 or 12 metal halide compound;

a2) forming a (pentafluorophenyl) Group 11 or 12 metal compound by decarboxylation of the Group 11 or 12 metal pentafluorobenzoate;

b) contacting the (pentafluorophenyl) Group 11 or 12 metal compound from step a2) with a boron halide compound to form tris(pentafluorophenyl)borane; and c) recovering the resulting tris(pentafluorophenyl)borane.

Preferred Group 11 or 12 metal oxides and hydroxides for use herein include zinc, copper, cadmium and mercury compounds. Highly preferred metal oxides and hydroxides are zinc and copper oxides and hydroxides. The most highly preferred metal oxides and hydroxides are zinc hydroxide or zinc oxide.

Preferred Group 11 or 12 metal halides for use herein include zinc, copper, cadmium and mercury compounds. Highly preferred metal halides are zinc and copper halides. The most highly preferred metal halide is zinc chloride.

Preferred Group 1 or 2 metal salts include lithium, sodium, potassium and magnesium compounds.

Step a1) is preferably conducted in the presence of a solvent or diluent at a temperature from 0° to 150° C., more preferably from 25° to 100° C. A preferred diluent is water. Any suitable pressure may be employed from 0.00001 to 1000 Mpa. The water used as a diluent or generated in step a1) may be removed (dehydration) by evaporation or by use of azeotropic distillation techniques, including reduced pressure, if desired. The decarboxylation reaction, step a2) can be conducted in the absence of a solvent or diluent, that is by sublimation, preferably under reduced pressure at temperatures of greater than 175° C., preferably greater than 190° C., most preferably greater than 200° C. Upper temperatures of the reaction are determined by safety and practical concerns. Temperatures less than 500° C., preferably less than 300° C. and most preferably less than 250° C. are preferred. Preferred pressures are from 0.00001 to 1 kPa.

The use of a diluent instead of sublimation techniques for step a2) is preferred, especially preferred is the use of a hydrocarbon diluent. When a diluent is employed, the use of reduced pressures and the attendant complexity associated with that process can be avoided. In fact, elevated pressures may be utilized in order to retain the diluent in a liquid state. Preferred diluents are $C_{6-40}$ aliphatic or alicyclic or aromatic hydrocarbons, especially octane, nonane, decane, undecane, dodecane, tridecane, tetradecane, decahydronaphthalene, tetramethylbenzene, pentamethylbenzene, hexamethylbenzene, diethylbenzene, diethyltoluene, triethylbenzene, triisopropylbenzene, and mixtures thereof.

Step b) may be conducted in the same diluent as was used for step a), or if no diluent was employed for step a), a diluent preferably is used for step b). Hydrocarbon diluents are preferred, but other solvents, for example ethers, may also be used provided that the solvents do not adversely affect either the starting materials or the product. The embodiment of the invention using ether diluents generally gives results inferior to the embodiment using hydrocarbon diluents. Of the ether solvents, strongly coordinating ethers such as tetrahydrofuran have been found to produce the best yields. The resulting adducts may be "cracked" to remove ether by contacting the complexes with a strong Lewis acid, especially $AlCl_3$ or $BCl_3$. Preferred boron halide compounds are boron trihalides, preferably boron trichloride. Step b) is preferably conducted at a temperature from 0° to 150° C., more preferably from 25° to 100° C. Any suitable pressure may be employed from 0.00001 to 1000 Mpa.

Preferably, the same diluent is utilized in steps a2) and b). Merely increasing the temperature, optionally the pressure, and periodically or continuously venting the reactor can be utilized in the subsequent decarboxylation process. Reduced or elevated pressures from 0.001 atmosphere to 100 atmospheres (0.0001 to 10 Mpa) and removal of $CO_2$ from the reactor such as by venting the same are desirably employed. The final recovery of tris(pentafluorophenyl)borane can be accomplished merely by decanting the solution of the reaction product from insoluble byproducts or coproducts or incompletely-reacted insoluble starting materials, by filtering or by a solvent exchange. If the tris(pentafluorophenyl) borane is desired in the absence of a solvent, the solvent may be readily removed by evaporation. In polymerization processes the presence of the hydrocarbon diluent is highly desirable and recovery of the final product in a neat form is not necessary.

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis.

EXAMPLE 1

Preparation of Zinc pentafluorobenzoate, $Zn(C_6F_5COO)_2$

Zinc pentafluorobenzoate, $Zn(C_6F_5COO)_2$, was prepared substantially according to the literature method, *Chem. Bet.* 1967, 100, 3016–3023, by reacting 4.76 g of zinc hydroxide with 20.3 g of pentafluorobenzoic acid in about 400 mL of boiling water. The resulting clear solution was concentrated to dryness while warming under reduced pressure. About 40 mL of water were added. After stirring for approximately 16 hours, the slurry was filtered and the product on the filter was washed two times with water, then dried under reduced pressure. The filtrate was concentrated to dryness. $^{19}F$ NMR spectra showed the presence of a small amount of pentafluorobenzoic acid in the filtrate product, but none in the material collected on the frit. This latter product was used in all subsequent reactions utilizing zinc pentafluorobenzoate.

Bis(pentafluorophenyl)zinc, $Zn(C_6F_5)_2$

Zinc pentafluorobenzoate (0.50 g) was slurried in about 10 mL of tridecane and the mixture was heated for several days after which time most of the solid has dissolved and the slurry had darkened. By observing the $^{19}F$ NMR spectrum, the reaction was deemed to be complete and to have formed the desired product. The bis(pentafluorophenyl)zinc was divided into two volumes for further use.

Tris (pentafluorophenyl)borane, $(C_6F_5)_3B$

To a portion of the previously prepared $Zn(C_6F_5)_2$-containing solution was added $BCl_3$ (1.0 M) in heptane to give a molar ratio of $B:(C_6F_5)$ of 1:3. A precipitate gradually formed. $^{19}F$ MR analysis showed the starting material was consumed and only peaks attributable to trispentafluorophenyl borane were present in the resulting liquid.

What is claimed is:

1. A process for preparing tris(pentafluorophenyl)borane, the steps of the process comprising:

a) forming a pentafluorophenyl metal compound wherein the metal is selected from Group 11 or 12;

b) contacting the (pentafluorophenyl) metal compound from step a) with a boron halide compound to form tris(pentafluorophenyl)borane; and c) recovering the resulting tris(pentafluorophenyl)borane.

2. A process according to claim 1 wherein step a) is performed by contacting pentafluorobenzoic acid with a Group 11 or 12 metal oxide or hydroxide under dehydration and, optionally, neutralization conditions, or by contacting a Group 1 or 2 metal salt of pentafluorobenzoic acid with a Group 11 or 12 metal halide compound under dehydration and, optionally, neutralization conditions, and decarboxylating the resulting product to form the corresponding pentafluorophenyl Group 11 or 12 metal salt.

3. A process according to claim 1 wherein step a) is performed in a hydrocarbon liquid at a temperature from 150° to 500° C.

4. A process according to claim 1 wherein step a) is performed by contacting a Group 11 or 12 metal chloride compound with a Group 1 or 2 metal salt of pentafluorobenzoic acid.

5. A process according to claim 1 wherein step a) is performed by contacting zinc oxide or hydroxide with pentafluorobenzoic acid.

6. A process according to claim 1 wherein steps a) and b) are performed in a hydrocarbon diluent.

7. A process according to claim 6 wherein the hydrocarbon diluent is a $C_{6-40}$ aliphatic or alicylic hydrocarbon or mixture of hydrocarbons.

8. A process according to claim 1 wherein the boron halide compound used in step b) is boron trichloride.

9. A process according to claim 1 wherein steps a) and b) are performed in a single reactor.

10. A process according to claim 1 comprising:

a1) forming a Group 11 or 12 metal pentafluorobenzoate by contacting pentafluorobenzoate acid with a Group 11 or 12 metal oxide or hydroxide under dehydration and, optionally, neutralization conditions, or by contacting a group 1 or 2 metal salt of pentafluorobenzoic acid with a Group 11 or 12 metal halide compound under dehydration and, optionally, neutralization conditions;

a2) forming a (pentafluorophenyl) Group 11 or 12 metal compound by decarboxylation of the Group 11 or 12 metal pentafluorobenzoate;

b) contacting the (pentafluorophenyl) Group 11 or 12 metal compound from step a) with a boron halide compound to form tris(pentafluorophenyl)borane; and c) recovering the resulting tris(pentafluorophenyl)borane.

* * * * *

UNITED STATES PATENT AND TRADEMARK OFFICE
CERTIFICATE OF CORRECTION

PATENT NO. : 5,744,646
DATED : April 28, 1998
INVENTOR(S) : David R. Wilson, et al.

It is certified that error appears in the above-identified patent and that said Letters Patent is hereby corrected as shown below:

On the title page, item [56], add the following:

OTHER DOCUMENTS

| | | |
|---|---|---|
| | | Chem. Ber., 100, 3016-3023, (1967) |
| | | Organometal. Chem. Rev., 1, 279-304, (1966) |
| | | Chem. Ber., 100, 2306-2311, (1967) |

Signed and Sealed this

Ninth Day of February, 1999

Attest:

Attesting Officer

*Acting Commissioner of Patents and Trademarks*